(12) United States Patent
Chen et al.

(10) Patent No.: US 9,339,614 B2
(45) Date of Patent: May 17, 2016

(54) FILTERING POWDER MEDICAMENT INHALER AND APPLICATION

(76) Inventors: Qingtang Chen, Zhejiang (CN); Xin Chen, Jiangsu (CN)

( * ) Notice: Subject to any disclaimer, the term of this patent is extended or adjusted under 35 U.S.C. 154(b) by 220 days.

(21) Appl. No.: 13/994,760

(22) PCT Filed: Dec. 15, 2011

(86) PCT No.: PCT/CN2011/084071
§ 371 (c)(1),
(2), (4) Date: Jun. 17, 2013

(87) PCT Pub. No.: WO2012/079525
PCT Pub. Date: Jun. 21, 2012

(65) Prior Publication Data
US 2013/0276783 A1    Oct. 24, 2013

(30) Foreign Application Priority Data
Dec. 17, 2010    (CN) .......................... 2010 1 0596113

(51) Int. Cl.
| | | |
|---|---|---|
| *A61M 11/00* | (2006.01) | |
| *A61M 15/00* | (2006.01) | |
| *A61M 15/08* | (2006.01) | |

(52) U.S. Cl.
CPC ......... *A61M 15/0028* (2013.01); *A61M 15/003* (2014.02); *A61M 15/0035* (2014.02); *A61M 15/0041* (2014.02); *A61M 15/08* (2013.01); *A61M 11/003* (2014.02); *A61M 2202/064* (2013.01)

(58) Field of Classification Search
CPC ................... A61M 2202/064; A61M 15/0028; A61M 15/0086; A61M 2206/16; A61M 15/0021; A61M 15/0041; A61M 15/00; A61M 15/08; A61M 11/003; A61M 15/003; A61M 15/0035
USPC ...................................................... 128/203.15
See application file for complete search history.

(56) References Cited

U.S. PATENT DOCUMENTS

| | | | | |
|---|---|---|---|---|
| 3,837,341 | A * | 9/1974 | Bell ........................... | 128/203.15 |
| 3,991,761 | A * | 11/1976 | Cocozza ................... | 128/203.15 |
| 4,249,526 | A * | 2/1981 | Dean et al. ............... | 128/203.15 |
| 2006/0254583 | A1* | 11/2006 | Deboeck et al. ......... | 128/203.15 |
| 2011/0005523 | A1* | 1/2011 | Lalor et al. ............... | 128/203.15 |
| 2013/0255679 | A1* | 10/2013 | Andrade et al. ......... | 128/203.15 |
| 2013/0269695 | A1* | 10/2013 | Brouet et al. ............ | 128/203.15 |

* cited by examiner

*Primary Examiner* — Steven Douglas
(74) *Attorney, Agent, or Firm* — George G. Wang; Bei & Ocean

(57) ABSTRACT

A filtering powdered medicament inhaler comprising a base (1) and an upper base (2). The upper base (2) has arranged therein a separator (62), which is connected at the bottom to a pressure groove (63). The upper base (2) has arranged thereon a hollow tube exterior connector (10) matching a suction tube (131). The hollow tube (19a) and a cavity (9) on one side of the separator (62) are interconnected via conduit (18), or, the hollow tube (19a) is extended for about 8 centimeters to form a mouthpiece. The upper base (2) has arranged in the cavity (9) thereof a filter (121). The base (1) is provided with an external base cover (72) which covers a press-button (5a) so as to reduce air flow into the cavity (9). The medicament inhaling conduit of the inhaler is relatively sealed and allows for rapid entrainment of a sufficient dosage of powdered medicament.

4 Claims, 7 Drawing Sheets

US 9,339,614 B2

FILTERING POWDER MEDICAMENT INHALER AND APPLICATION

FIELD OF THE INVENTION

This invention relates to a medical apparatus, especially a filtering powder medicament inhaler and its application, specifically, an inhaler for either standalone use or for use in conjunction with a powder medicament mouthpiece.

BACKGROUND OF THE INVENTION

Presently, there are a number of models of dry powder inhalers being used to treat asthma, but the curing rate by the GINA standard is only about 5%. The powder medicament particles for inhalation can easily agglomerate and are difficult to separate. The dosage is low and thus packaging is difficult. Therefore, it is usually mixed with a large amount of lactose, as high as 98.8% of the total volume of dry powder. However, long-term inhalation of lactose can produce side effects. If the amount of the lactose inhalation is to be reduced, the dosage of dry powder has to be reduced, resulting in lower efficacy of treatment.

SUMMARY OF THE INVENTION

The object of the present invention is to separate the active powder medicament from dry powder composition to allow quick inhalation of a sufficient dosage and removal of lactose, for enhancing the efficacy.

Technical Solution

The object of this invention is realized in the following way: a filtering powder medicament inhaler, comprising of the base (1) and upper base (2); inside the base (1) is provided with a capsule chamber (4), the chamber lower side (81) is a half-moon-shaped groove upward, on both sides of the chamber are provided with triangle piercing knives (6), respectively provided with pushbutton (5), pushbutton (5a) and return spring; the upper base (2) is pivot mounted on the base (1) via the shaft in the opening (64) on one side, and can close or open with the base (1) with the positioning hook (2a) on the other side; at the mouth of conduit (18) in upper base (2) there is a fence, with the features that:

a) In the upper base (2) there is a separator (62), its lower end is connected with groove (63), the groove lower side (82) is downward half-moon-shaped;

b) The upper base (2) has arranged thereon a hollow tube exterior connector (10) matching a suction tube (131), the hollow tube (19a) and a cavity (9) on one side of the separator (62) are interconnected via conduit (18), or, the hollow tube (19a) is extended for about 8 centimeters to form a mouthpiece;

The upper base (2) has arranged in the cavity (9) thereof a filter (121);

The base (1) is provided with an external base cover (72), with square frames (73) on the façade, which covers a press-button (5a) so as to reduce air flow into the cavity (9), and relatively seal the inhaling conduit and allow for rapid entrainment of powdered medicament.

In this invention, multiple suction tubes including suction tube (131) and suction tube (132) connected with each other are connected to form the mouthpiece, or the suction tube (131) is connected with at least two small suction tubes (131a) to form the mouthpiece; or the inside of suction tube contains a filter (121) including the filter cup, for which the number, shape, size and layers of filtering pores are set as required, for example to stop particles sized over 6 μm.

In this invention: the hollow tube (19a) contains the intubation tube (67), ball (68) and fence.

In this invention: the upper base (2) is provided mouthpiece cover (71), which covers the suction tube (131), on a drug storing chamber (74) is arranged on the mouthpiece cover (71).

Beneficial Results:

The advantage of this invention is: the base cover (72) relatively seals the inhaling conduit, so that the dry powder can be quickly carried out and powder medicament is filtered out when the air flows though the capsule during inhaling, allowing entrainment of sufficient powdered medicament in the first time, with significant efficacy.

DETAILED DESCRIPTION OF PARTICULAR EMBODIMENTS OF THE INVENTION

In the following, this invention is further described in conjunction with attached drawings.

Figure 1:
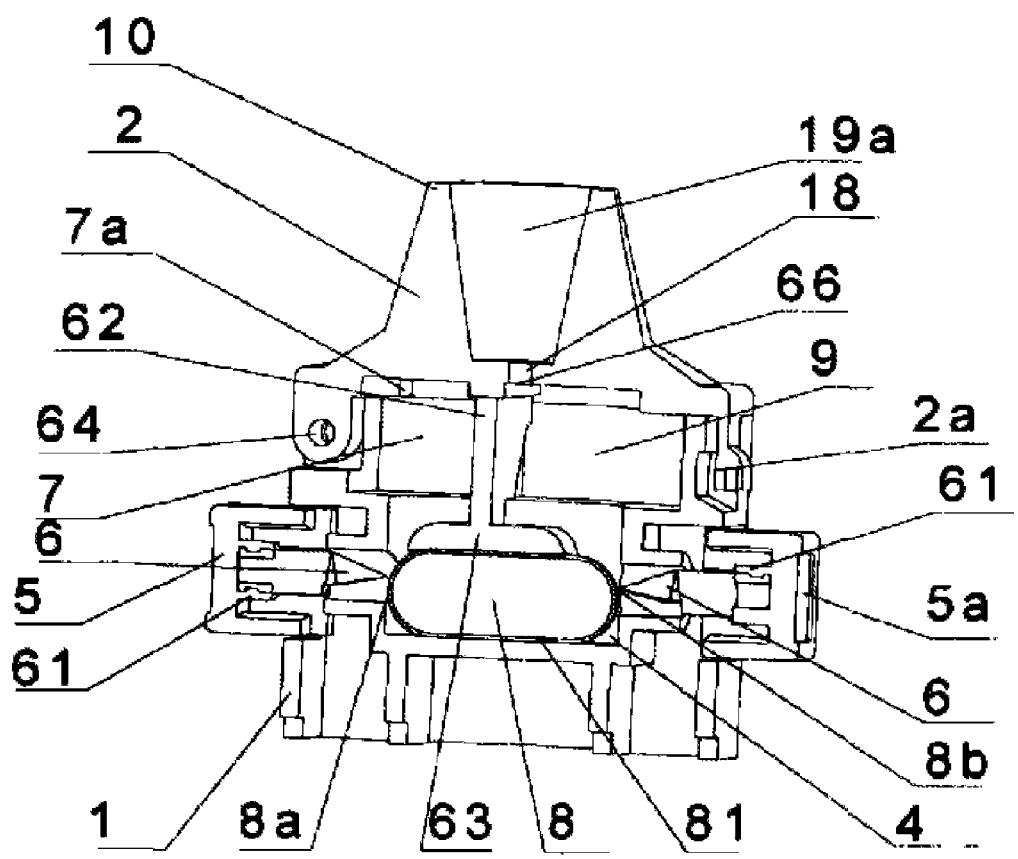
FIG. 1 is the sectional schematic diagram of the base (1) and upper base (2) of this invention.
Figure 2:
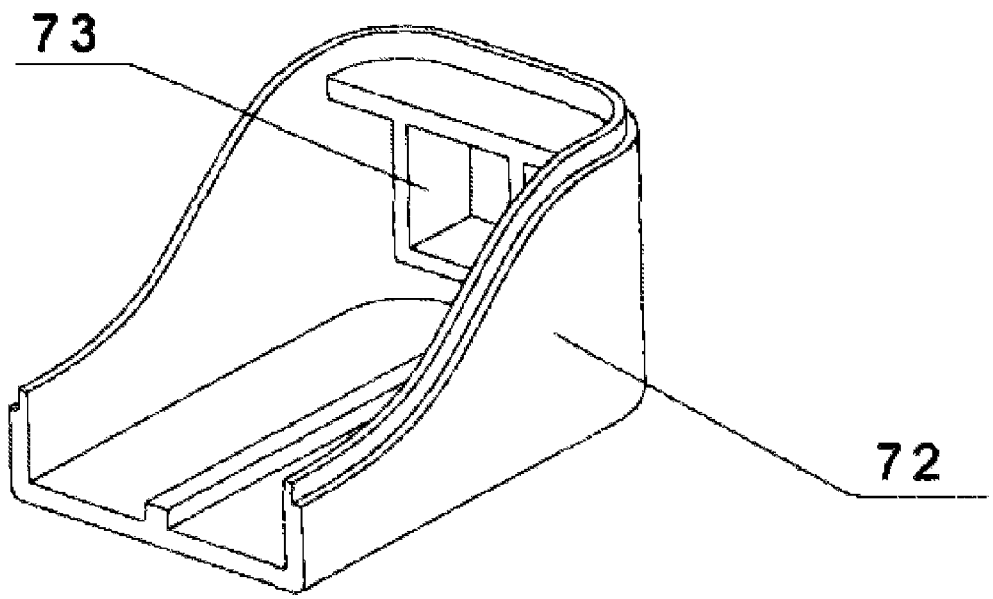
FIG. 2 is the schematic diagram of the base cover (72) of this invention
Figure 3:
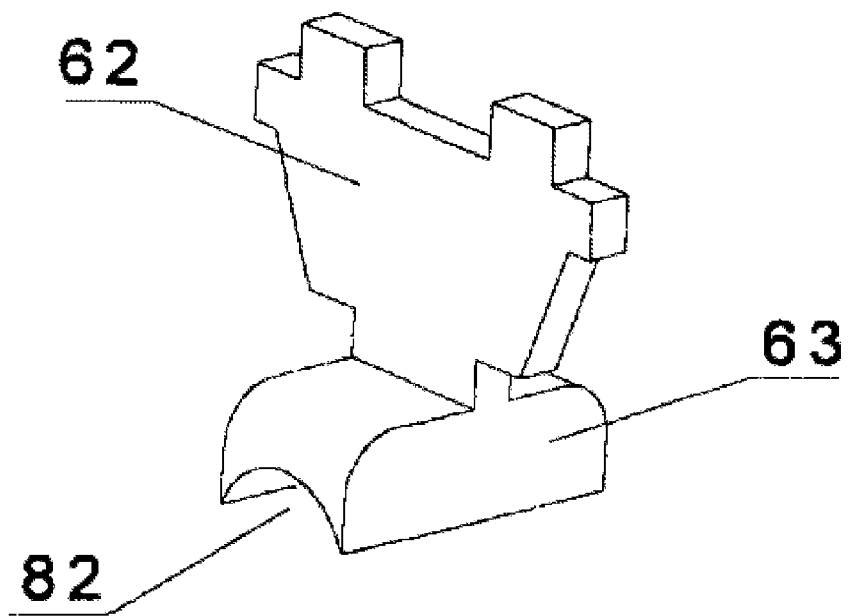
FIG. 3 is the inclined schematic diagram of the separator (62) in upper base (2) and the groove (63) of this invention.
Figure 4:
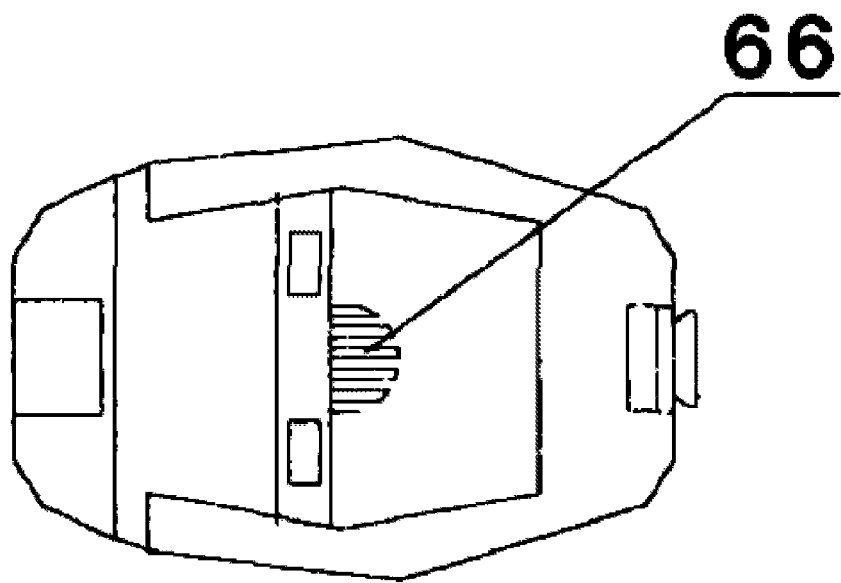
FIG. 4 is the upward schematic diagram of the upper base (2) of this invention.
Figure 5:
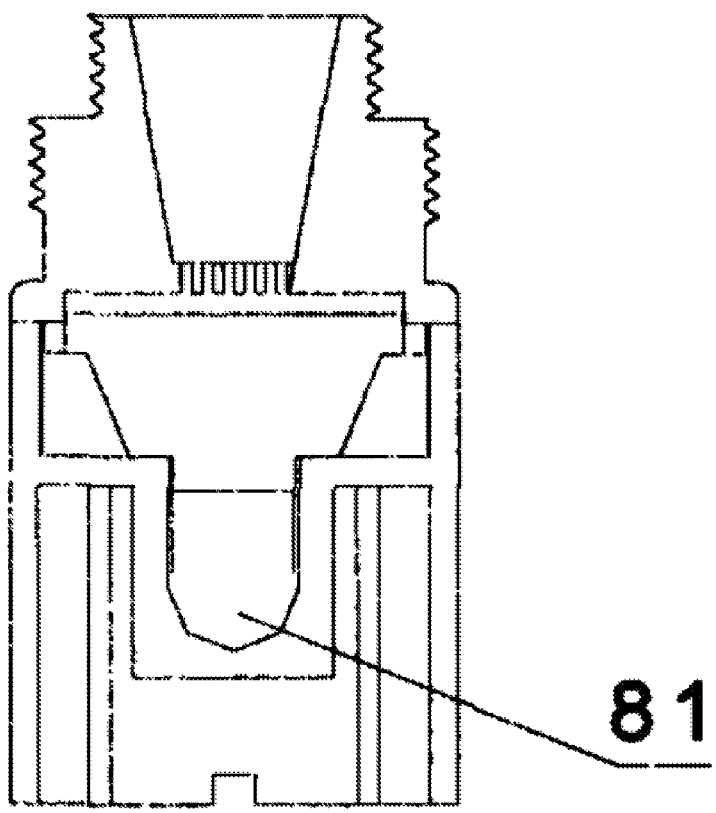
FIG. 5 is the longitudinal sectional schematic diagram of the base (1) and upper base (2) of this invention.
Figure 6:
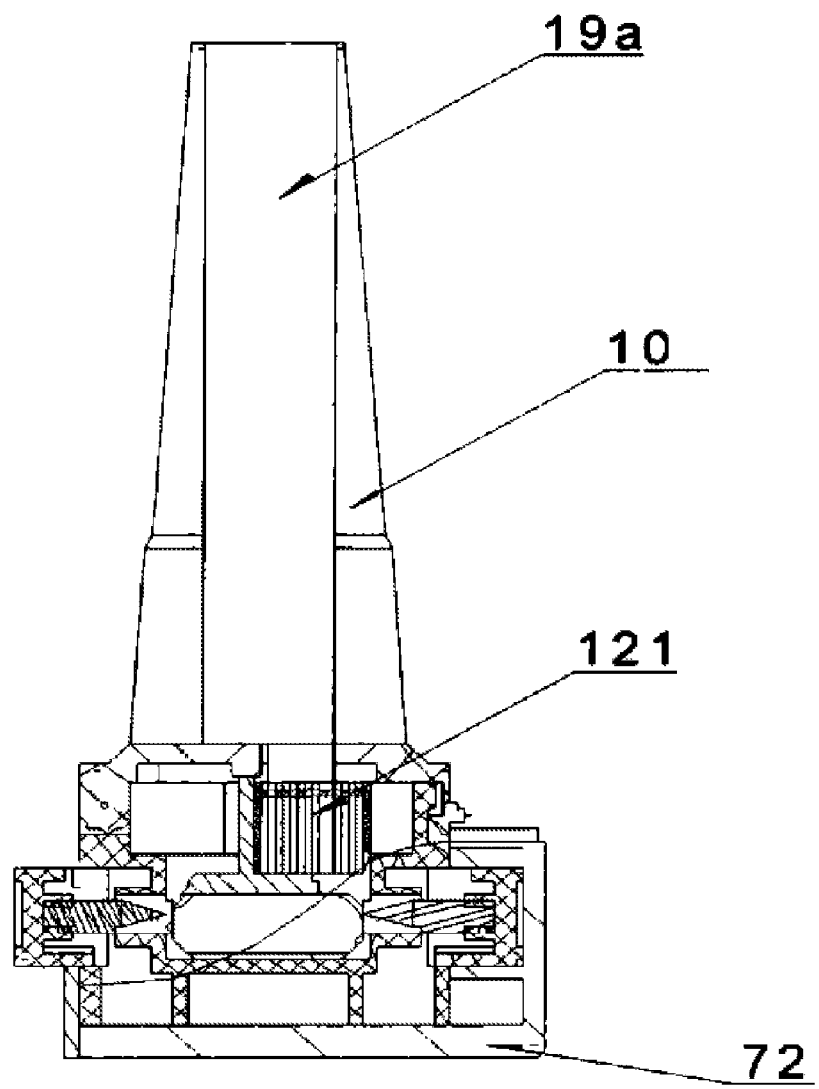
FIG. 6 is the sectional schematic diagram of the mouthpiece formed by the extension of the base cover (72) and hollow tube (19a) outside the base (1) of this invention.
Figure 7:
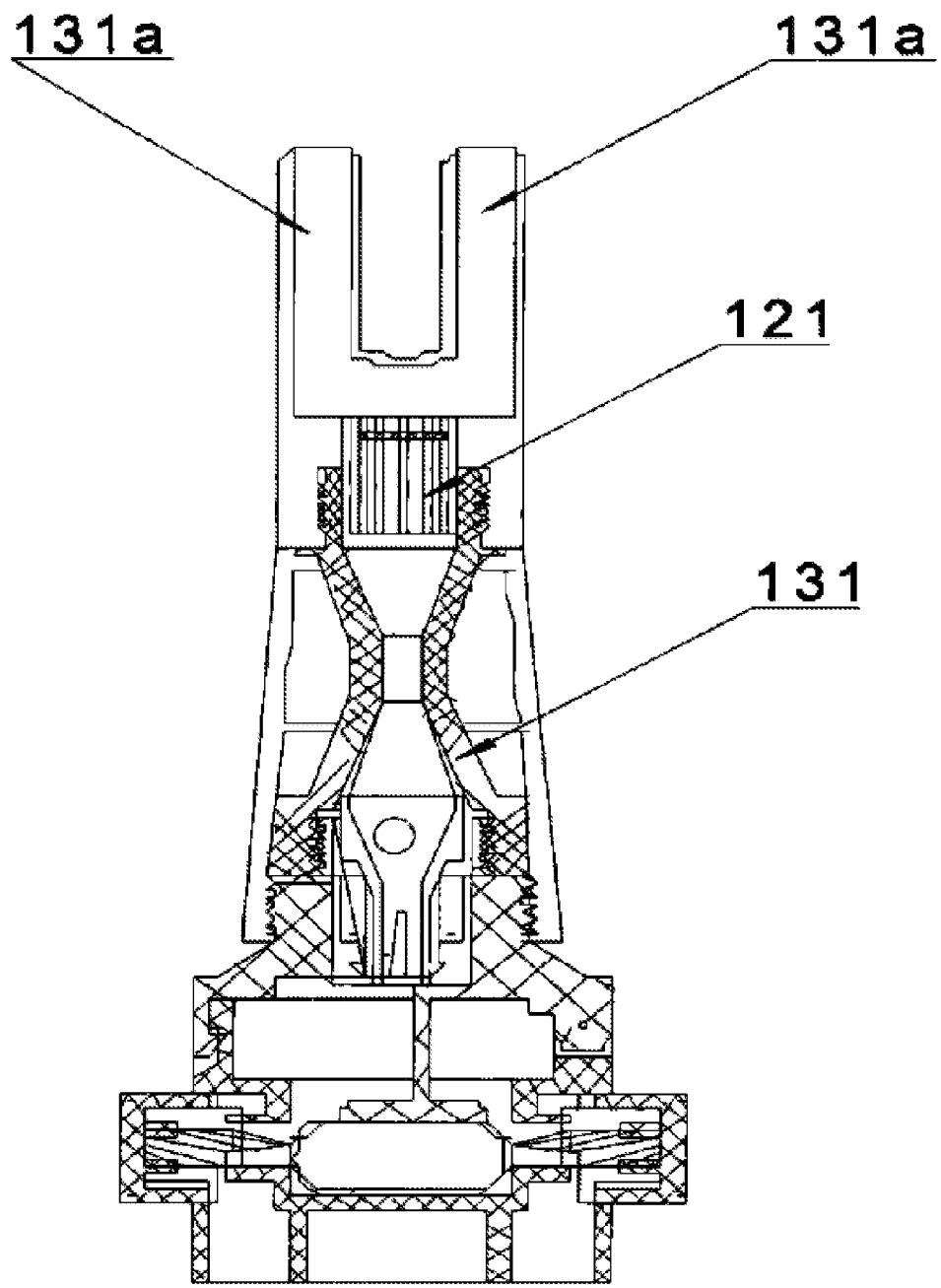
FIG. 7 is the sectional schematic diagram of the two small suction tubes (131a) on suction tube (131) for nose application of this invention.
Figure 8:
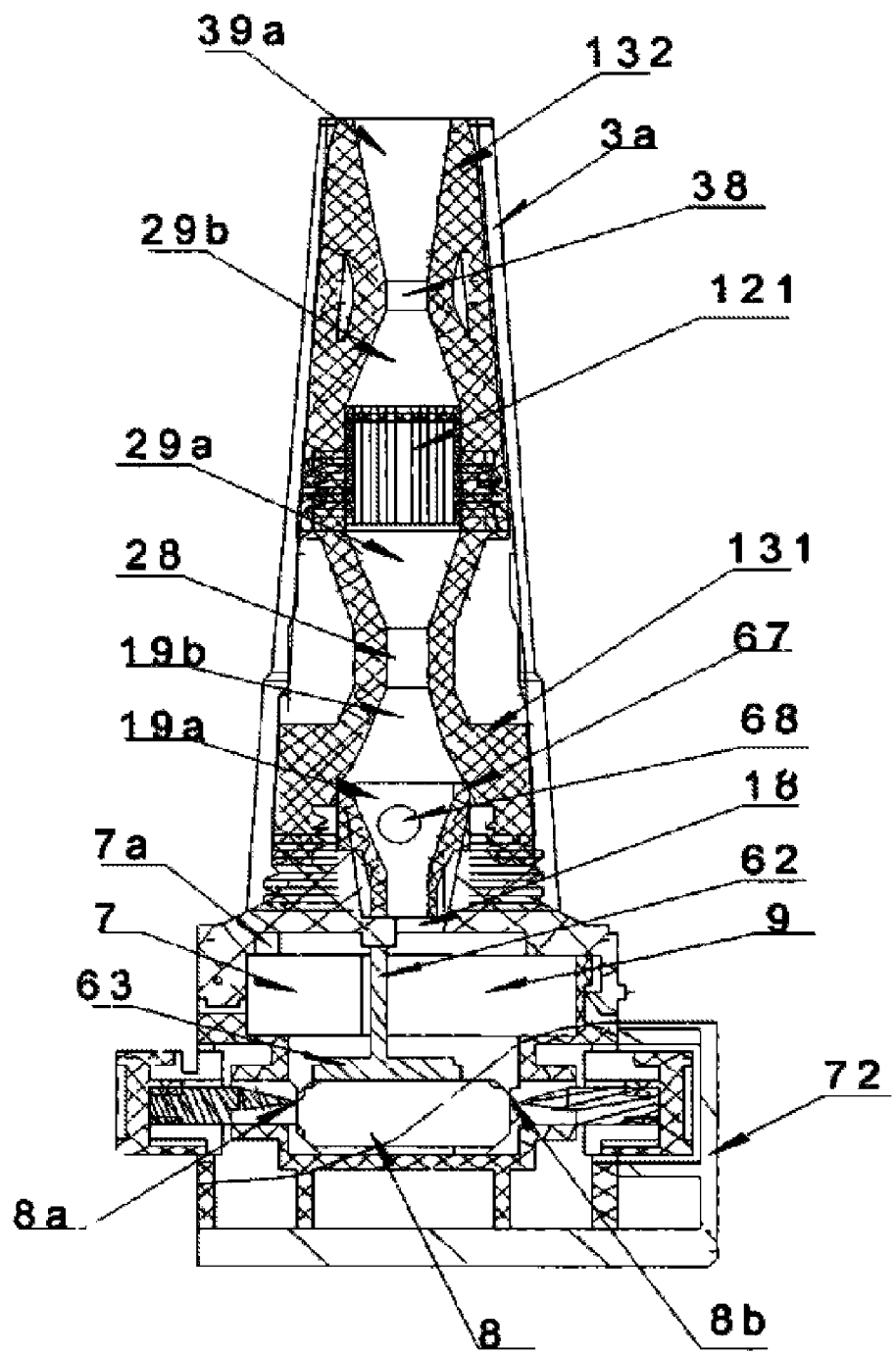
FIG. 8 is the butt connection schematic diagram of the upper base (2) with suction tubes (131 and 132) and mouthpiece outer sleeve (3a) of this invention.
Figure 9:
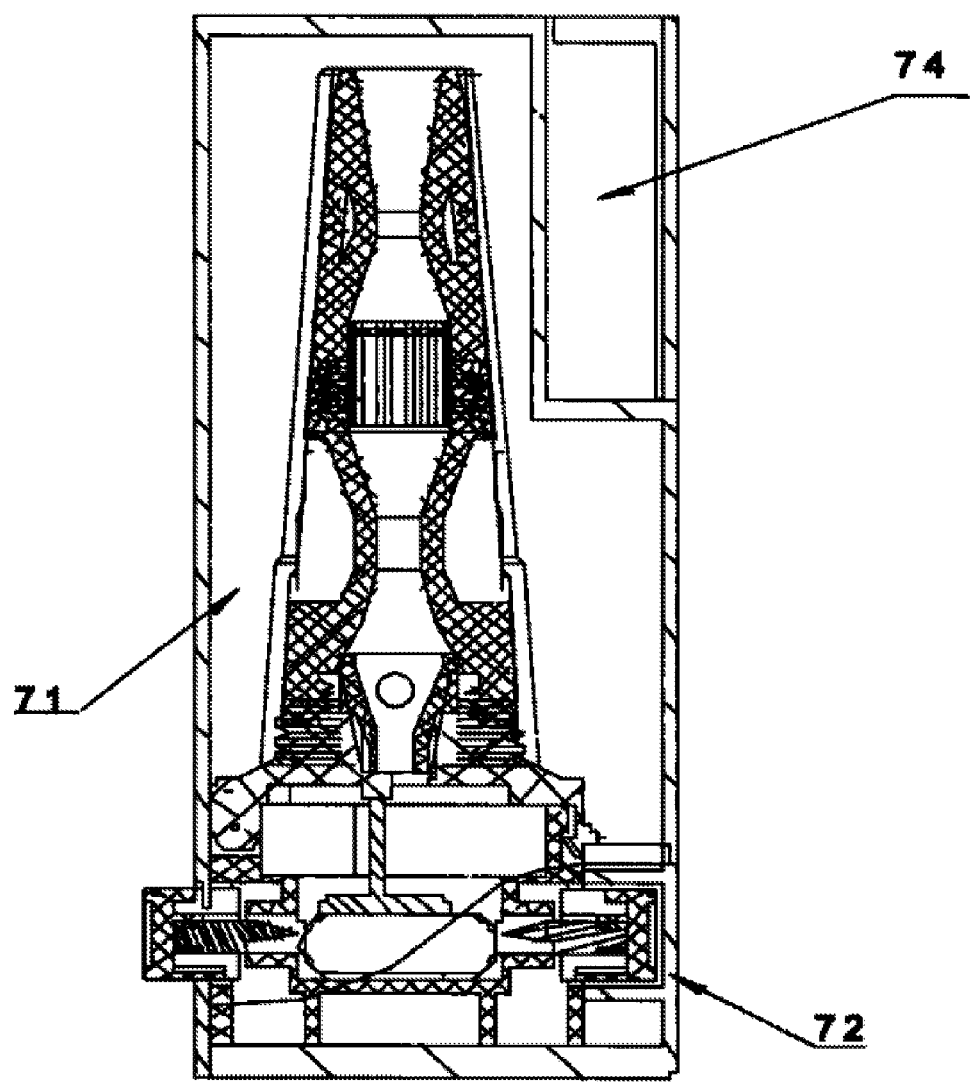
FIG. 9 is the schematic diagram of the mouthpiece cover (71) on the upper base (2) and the drug storing chamber (74) of this invention.

Embodiment 1:

A filtering powdered medicament inhaler (FIG. 6) is comprised of a base (1) and an upper base (2). The hollow tube of upper base (2) is extended by about 8 cm as the mouthpiece, the tube cavity (19a) is the powder medicament inhale outlet; the cavity (9) inside upper base (2) is arranged with a filter bag (121). In use, the base cover (72) is first taken off, press the hook (2a) to open the upper base (2), put the capsule (8) into the capsule chamber (4), and then close the upper base (2) again on base (1). Then press with two fingers concurrently the two press-buttons (5 and 5a) to pierce the capsule, and then push the base cover (72) from the press-button (5a) side. When powder medicament is inhaled from the outlet (19a), air flows from inlet (7a) into the cavity (7)→the pierced break (8a) to inside the capsule (8), the air stream carries the dry powder from the pierced break (8b)→the filter bag in cavity (9), the lactose particles sized over 10 μm are stopped inside the filter bag, and powder medicament particles sized below 5 μm are quickly inhaled into the respiratory tract. After use, dismantle and clean the inhaler, and dry it up for later use.

Functions of the separator (62) and groove (63) in upper base (2): 1. separating the cavity in upper base (2) into cavities (7) and (9), so that air stream will carry dry powder mainly from the capsule to cavity (9); (2) pressing the capsule and squeezing the air inside the capsule to both ends, to facilitate piercing; and 3. the hand-contaminated surface of the capsule is pressed by the upper and lower grooves, to avoid contacting with the air stream and dry powder, to prevent cross infection.

Embodiment 2:

A filtering powder medicament inhaler (FIG. 8), with a filter bag (121) in the mouthpiece tube cavity. In cavity (19*a*), the intubation tube (67) and ball (68) can be placed, then the suction tube (131) is connected with hollow tube (10). In inhaling, the dry powder is vibrated by the ball (68), which collides the lactose particles to separate the powder medicament particles, to facilitate filtering. In case of accidental exhale into the inhaler, the ball (68) is blocked at the narrow part of the intubation tube to prevent powder medicament from blowing out of the device.

In the embodiments, the parts of this invention can be made by injection moulding or with metal and new materials. And the finished parts can be fitted and connected.

What is claimed is:

1. A filtering powder medicament inhaler having a first side and a second side, comprising a base (1) and an upper base (2); wherein inside the base (1) there is provided with a capsule chamber (4), which has a lower side (81) taking the form of an upward half-moon-shaped groove with two side walls (8*a* and 8*b*), which are each provided with a triangle piercing knife (6), together with a button selected from the group consisting of a first press-button (5) and a second press-button (5*a*) and a return spring; the upper base (2) is pivotally mounted on the base (1) via a shaft in an opening (64) on the first side of the inhaler, and can close or open the base (1) via a positioning hook (2*a*) on the second side of the inhaler; and at a mouth of a conduit (18) in the upper base (2) there is a fence; and wherein:

a) in the upper base (2) there is a separator (62) with a lower end connected with a groove (63), which has a downward half-moon shaped lower side (82);

b) the upper base (2) has arranged thereon a hollow tube exterior connector (10) matching a suction tube (131), and a hollow tube (19*a*) and a cavity (9) on one side of the separator (62) are interconnected via a conduit (18);

c) the upper base (2) has a filter (121) arranged in the cavity (9);

d) the base (1) is provided with an external base cover (72), which covers the press-button (5*a*) so as to reduce air flow into the cavity (9), and relatively seal an inhaling conduit and allow for rapid entrainment of powdered medicament.

2. The filtering powder medicament inhaler of claim 1, further comprises at least a first suction tube and a second suction tube, wherein the first suction tube (131) and the second suction tube (132) are interconnected to form a mouthpiece; or the first suction tube (131) is connected with at least two small suction tubes (131*a*) to form a mouthpiece; or the first suction tube contains a filter including a filter cup with filtering pores, of which the number, shape, size and layers are set as required to stop particles of particular sizes.

3. The filtering powder medicament inhaler of claim 1, wherein the hollow tube (19*a*) contains an intubation tube (67), a ball (68) and a fence.

4. The filtering powder medicament inhaler of claim 1, wherein the upper base (2) is provided with a mouthpiece cover (71), which covers the suction tube (131), and has a drug storing chamber (74) arranged thereon.

* * * * *